(12) United States Patent
Lundström et al.

(10) Patent No.: US 6,187,597 B1
(45) Date of Patent: Feb. 13, 2001

(54) DEVICE FOR THE EXPANSION OF SENSOR SELECTIVITY

(75) Inventors: Ingemar Lundström, Linköping; Hans Sundgren, Vikingstad, both of (SE)

(73) Assignee: Nordic Sensor Technologies AB (SE)

(*) Notice: Under 35 U.S.C. 154(b), the term of this patent shall be extended for 0 days.

(21) Appl. No.: 09/000,134

(22) PCT Filed: Jul. 4, 1996

(86) PCT No.: PCT/SE96/00908

§ 371 Date: Jan. 23, 1998

§ 102(e) Date: Jan. 23, 1998

(87) PCT Pub. No.: WO97/05476

PCT Pub. Date: Feb. 13, 1997

(30) Foreign Application Priority Data

Jul. 25, 1995 (SE) .................................................. 9502688

(51) Int. Cl.$^7$ .................................................. G01N 1/22
(52) U.S. Cl. .................. 436/181; 422/98; 436/149; 436/152
(58) Field of Search .................. 422/98; 436/149, 436/152, 37, 181; 204/400

(56) References Cited

U.S. PATENT DOCUMENTS

| | | | |
|---|---|---|---|
| 2,857,251 | * 10/1958 | Krogh | 436/152 |
| 3,595,621 | * 7/1971 | Andreatch | 436/152 |
| 4,169,126 | * 9/1979 | Iles | 422/98 |
| 4,584,867 | 4/1986 | Forster . | |
| 4,885,929 | 12/1989 | Kasahara et al. . | |
| 4,992,384 | 2/1991 | Laurs et al. . | |
| 5,545,377 | * 8/1996 | Fukaya et al. | 436/37 |
| 5,693,877 | * 12/1997 | Ohsuga et al. | 436/37 |

FOREIGN PATENT DOCUMENTS

| | | |
|---|---|---|
| 665908 | 6/1988 | (CH) . |
| 0305963 | 3/1989 | (EP) . |

OTHER PUBLICATIONS

Schweizer–Berberich et al, Characterisation of Food Freshness with Sensor Arrays, Sensors and Actuators, vol. 18–19, 1994, pp. 282–290.

* cited by examiner

*Primary Examiner*—T. Tung
(74) *Attorney, Agent, or Firm*—Hayes, Soloway, Hennessey, Grossman & Hage PC

(57) ABSTRACT

Electronic odor detecting device (electronic nose) provided with a number of sensors. The gas that is to be subjected to the detection is brought to pass a number of similar or different sensors distributed on a surface. Between the sensors or actually extending between and past the sensors is a catalyst. The catalyst may be arranged on an opposing wall in a detection cell or in the same surface as the sensors. Constituents of the gas that react with the catalyst result in a different signal pattern for the sensors, depending on their location in relation to the catalyst. Since different substances in the gas will react with different rates in the presence of the catalyst, the sensed pattern will change along the catalytic surface. This makes it possible to evaluate a gas mixture with great precision and with a more limited number of sensors in comparison to prior art. In order to enhance the selectivity of the different sensors, the catalytic surface may also be held at different temperatures at different areas of the measurement cell. In the same cell also patterned catalytic surfaces may be arranged.

6 Claims, 4 Drawing Sheets

DEVICE FOR THE EXPANSION OF SENSOR SELECTIVITY

BACKGROUND OF THE INVENTION

Gas sensors sensitive to different molecules are known. Such sensors are normally not totally selective but have different selectivity patterns. It is known to combine such sensors in order to analyze gas mixtures and odors. By comparing the obtained response patterns with previous test results using a computer remarkably precise results can be obtained regarding the identification, classification and also quantification of gas mixtures and odors.

The combination of a number of sensors and a pattern recognition routine is known as an "electronic nose" [Sensors and Sensory Systems for an Electronic Nose, (J. W. Gardner and P. N. Bartlett, eds.) Nato ASI Series E, vol. 212, Kluwer Academic Publishers, 1992]. Electronic noses have numerous applications within the and food processing industry, medical diagnosis, control of combustion, processes and monitoring of the environment, to mention a few.

Modern computers have improved upon the use of pattern recognition methods to identify the response pattern from different sensor to different odors. Many different sensors are available and in many cases a number of set ups may have to be tested and even combined to provide a correct analysis in the end. This is particularly important since it is not only desirable to know which molecules, but it is also in many cases important to know their actual concentrations. This presents a problem since the sensors may have to detect very small quantities of material or very large quantities of the same. Sensors that are too sensitive will not be able to measure large quantities correctly and sensors that are not sensitive enough will not give any indication at all of low concentrations. Thus, in order to obtain arcuate readings taking into consideration amount, concentration and identification, a versatile electronic nose sensor with a range of selectivities and sensitivities is necessary. Furthermore, the choice of the sensors will depend on the particular application. As a result of the above difficulties the electronic noses of today are not very versatile and may in some instances require very large number of sensors and data power making them rather expensive and slow.

Another problem encountered is the lack of selectivity, that is, many sensors react on many gases almost identically, making it difficult to tell them apart and necessitating additional sensors etc.

The object of the present invention is to provide a method by which the analyzing power of chemical sensor arrays can be expanded and a more exact as well as a more versatile device for the monitoring of gas mixtures and odors.

SUMMARY OF THE INVENTION

In accordance with the invention this is achieved by using a new sensing principle based on a geometrical distribution of sensors and catalysts. This arrangement gives a number of possibilities for the enhancement and control of the signal pattern from a sensor array for a given gas mixture.

In this new sensing method according to the invention the gas or gas mixture that is to be analyzed is brought to pass a catalyst simultaneously with detection by sensors. Many of the gas components that are desirable to monitor react in one way or the other in the presence of a catalyst. This means that the gas passing over the catalyst will change in its proportions of different molecules. This in turn can be detected since sensors placed along the catalyst will give different readings. Since different molecules react in different ways in the presence of a specific catalyst a recognizable pattern specific to the mixture will be obtained in the gas flow direction along the catalyst.

The sensors can be arranged in the catalyst itself, or catalysts and sensors may constitute for example, the top and bottom surfaces in a gas analyzing flow cell, provided that the height is not too large, since the change in the composition due to chemical reactions at the catalyst must also influence the sensors in order to provide the recognizable pattern. Such a measuring cell can be provided with a varying set up of catalysts or catalytic surfaces, and indeed several different catalytic materials can be used in, for instance, strips in the cell and also different sensors can be used. A set up change can however be obtained in other interesting ways. To start with, the thickness of the layers of catalytic materials can vary along the flow path. Also the temperature of the sensors and/or the catalytic materials may vary along the flow path or crosswise of the flow path in order to provide suitable recognizable patterns. The size of the catalytic areas and the temperature of these areas will influence the concentration/alteration of the gas components. The temperature at the sensors will influence the sensitivity of the sensors. Suitable catalytic materials are platinum, palladium, iridium as well as other organic or inorganic materials, including semiconducting materials.

The presence of a catalyst may change gas components that are not otherwise measurable with the sensors used into components that can be measured or sensed by the sensors. Conversely and at the same time, for example, other components that can be sensed can be changed into components that are not sensed by the used sensors if desired.

One of the major advantages of the invention is the above mentioned possibility to construct in a simple way sensor cells that can easily be switched between a number of different selectivity patterns. It gives the possibility to use a modular system comprising one or two dimensional sensor matrices or arrays and a catalytic surface or even an array of matrix of catalysts comprising areas of different catalytic materials that can be combined to give a device with a great number of different selectivity patterns. Top and bottom in an analyzing cell can be combined to provide the desired selectivity and sensitivity, which efficiently reduces the number of sensor arrays that has to be kept in store. Since the catalytic part (for instance top) need no or only few (temperature control) electrical connections, substitution can be carried out in simple mechanical ways. Further advantages and features of the invention are apparent from the following description of preferred embodiments.

BRIEF DESCRIPTION OF THE DRAWINGS

Further advantages and features of the invention are apparent from the following description of preferred embodiments described in connection with enclosed drawings wherein FIG. 1

DETAILED DESCRIPTION OF THE PREFERRED EMBODIMENT

Figure 1:
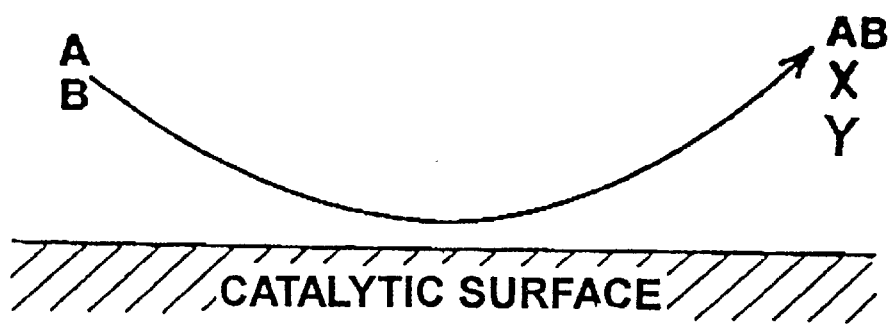
Figure 2:
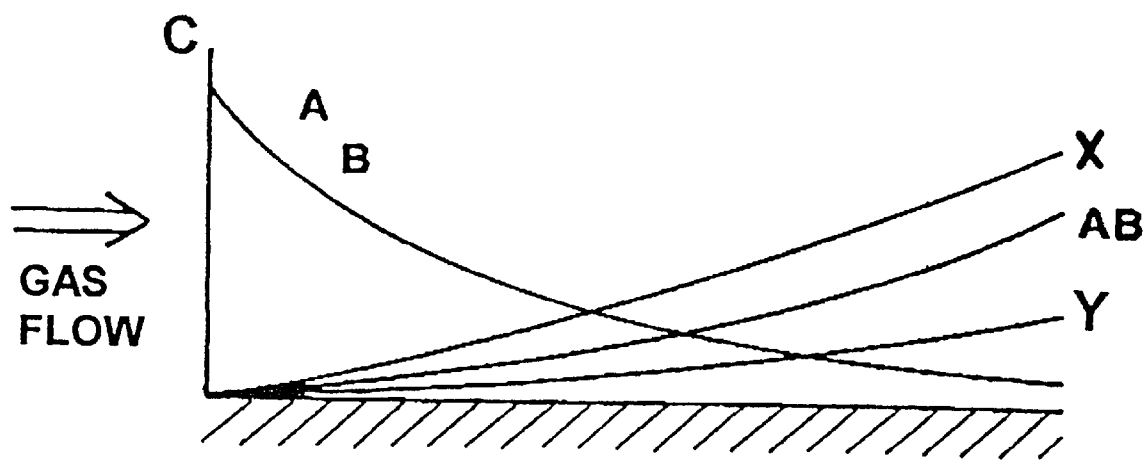
FIG. 2 is shown in schematic what happens when a gas passes a catalytic surface.
Figure 3A:
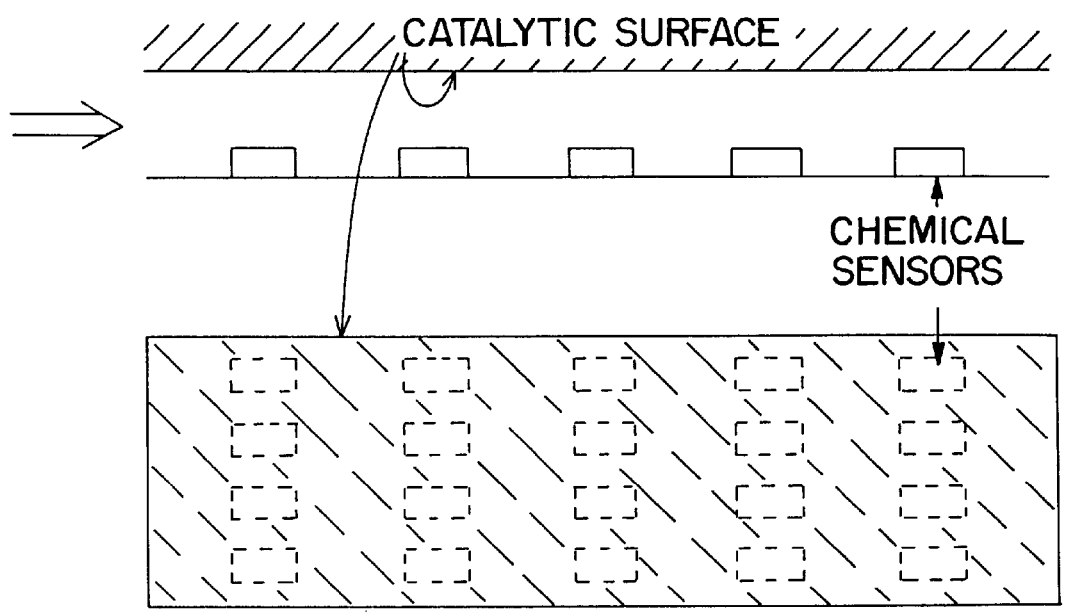
FIG. 3*a* shows a gas sensing cell.
Figure 3B:
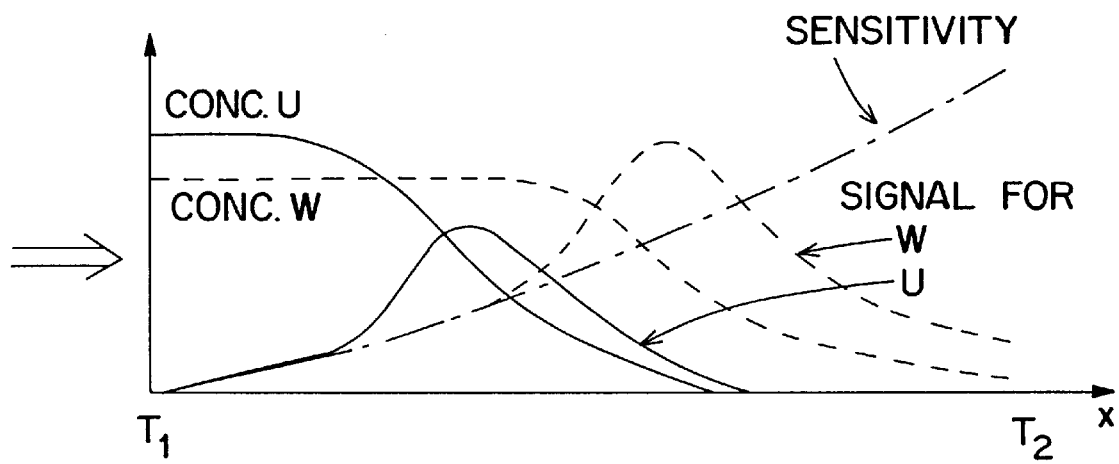
FIG. 3*b* shows an example of possible sensor signals.

The invention is based on the fact that catalytic materials (not only metals but also semiconductors, insulators organic materials, zeolites etc.) efficiently consume molecules and make new molecules by reactions on the surface of the material as it is schematically shown in FIG. 1. This means that if a stream of gas is passing over a catalytic surface the concentrations of gas components A and B are reduced while the concentrations of the reaction products AB, X and Y increase as shown in FIG. 2. This effect is used to analyze a gas mixture since the different parts of the mixture are used up/react with different rates along the surface. In FIG. 3b, this is depicted with two components U, W that when reacting in the presence of the catalytic surface give rise to the products S and P, respectively (only U and W are shown in FIG. 3b). As shown in FIG. 3a, by arranging the catalytic surface for instance on the top surface of the flow cell and placing chemical sensors along the bottom surface of the flow cell, sensitive to U, W, P and/or S, the reaction pattern can be measured and with this the composition of the gas mixture can be analyzed. This possibility is shown schematically in FIG. 3b. More complicated patterns are obtained if S and P can also be detected.

The flow cell in the device in FIG. 3a should be so thin that the consumption/making of molecules at the catalytic surface is observed also at the other wall of the flow cell with the chemical sensors. The distance is determined by for instance, flow rates, and the reactivity of the catalytic surface, and the available pressure differences between inlet and outlet of the flow cell. This distance however vary widely, but, for practical purposes is between 0:001 and 10 mm. The length of the flow cell is determined partly by the reactivity of the catalytic surface and of the number and type of chemical sensors that are placed along the channel. Lengths between 1–100 mm are therefore probable. The width of the flow cell is essentially dictated by the sensor technology that is used and of the total gas flow that is to be accommodated. The width however is not the critical parameter and therefore can also vary widely. In FIG. 3a is shown four sensor rows where each row can consist of sensors with the same or different selectivity patterns in relation to different types of gas or molecules.

If desirable the cell may also comprise walls separating the flow over different areas of sensors, coinciding with the strips of catalytic materials or more or less crosswise of these.

One of the unique features of the invention is the increased number of possible combination that can be achieved when the device according to FIG. 3a is used. The catalytic activity depends on choice of catalytic material and its temperature. Surfaces with "patterns" of consumption and production of molecules can therefore be fabricated. Many chemical sensors based for instance on semiconducting metal oxides, field effect transistors, etc. have a temperature dependent sensitivity and selectivity. By varying the temperature along the sensor matrices and/or the catalytic surface therefore a number of different response patterns can be obtained dependent upon the particular catalytic surfaces and sensor matrices.

FIG. 3b shows an example where a temperature gradient (T1<T2) exists along the sensor matrix and the catalytic surface and where the consumption of U and W on the catalytic surface increases with the temperature and where the sensitivity of the sensors for U and W also increases with the temperature. In this case, maxima of the response to U and W along the sensor matrix are obtained. The position of the maxima are in general different for U and W. An interesting observation is that the sensors in the example shown in FIG. 3b may be entirely unselective for U and W. Selectivity, however is provided by the catalytic consumption of the molecules.

Figure 4:
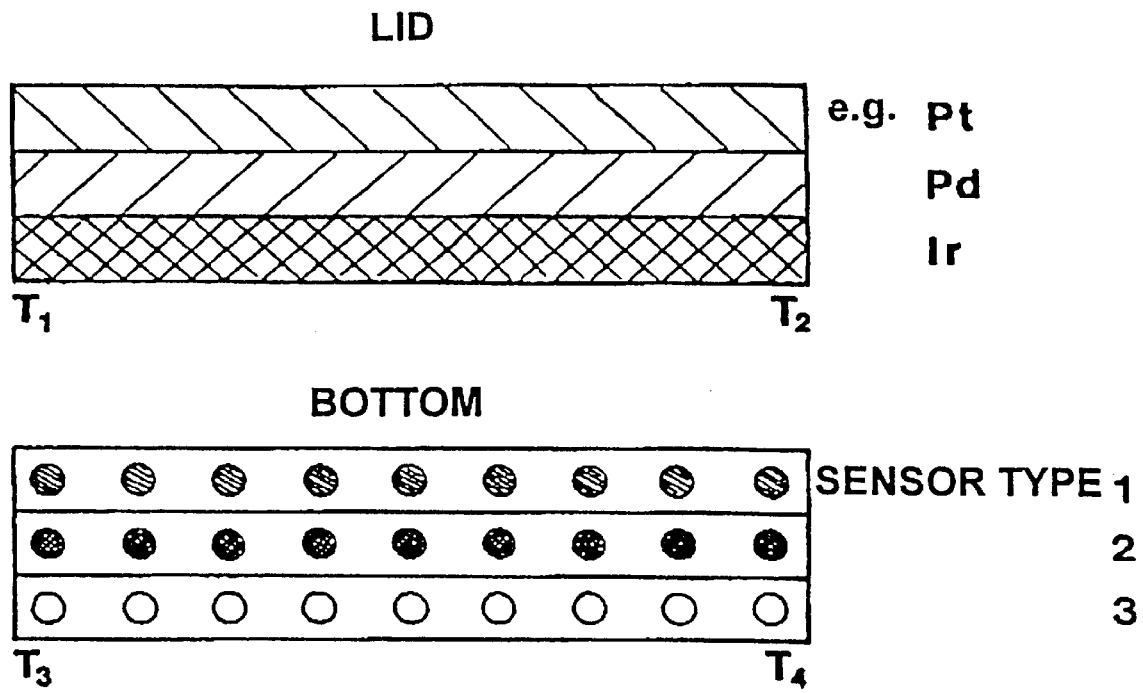
FIG. 4 shows the top and bottom of a cell with catalyst and sensor patterns respectively

It is apparent that the device in FIG. 3a can be given considerable analytic ability by for instance providing bands of catalytic materials with different selectivity/activity for different classes of molecules and providing areas or rows of chemical sensors with different selectivity patterns for different classes of molecules. FIG. 4 schematically illustrates these possibilities. The sensors can, for instance, be field effect transistors with a thin layer of platinum, a thick layer of palladium and a thin layer of iridium. Mixtures of sensor technologies can also be used, for instance, two rows with field effect transistors and one with semiconducting metal oxide (so called Taguchi-sensors). The areas of the sensors and the catalytic bands need not be overlapping but may be separated. FIG. 4 shows that one can also consider having different temperature gradients along the sensor areas and the catalytic surface. Rather than have the gradients along the areas or bands, another option regarding the temperature is to have the gradients in an angle in relation to the areas in bands.

The invention constitutes a great improvement over the prior art since it allows the use of sensors that cannot of themselves sense any difference between different molecules, but together with the arrangement of a catalyst, can. To start with molecules that do not react or do react in the presence of the catalyst will be appreciated immediately. However, even with molecules that do react at the same catalytic surface it will be possible to differentiate between them since the maximum of the response (signal) will be found at different locations in the cell, since they will react with different rates in the cell.

The invention also constitutes a great step forward as regards sensor elements for electronic noses since both the catalytic surfaces and the sensor areas can be standardized and need only to be combined to provide the final selectivity pattern. In an electronic nose it is required that the sensors provide signals, the patterns of which vary with the mixture of the blend of gases (odours). The device provided here is very useful. The device can be built in different ways. The sensor areas can be arranged in any angle in relation to the catalytic areas, which increase the number of possible selectivity patterns further. Sensors with different selectivity need not be arranged in rows but can be arranged in any two dimensional pattern. This also goes for the catalytic surface. Sensor and/or catalytic areas can be made on the same substrate or on separate substrates.

Catalytic metals such as palladium, iridium, platinum, ruthenium and alloys of them convert organic molecules with a rate that is ruled by the choice of metal and temperature. Sensors also exist for the majority of organic molecules, for instance field effect transistors with gates made of catalytic metals or sensors based on semiconducting metal oxides (SNO2, TiO2). Such sensors can be made small and with ease and placed in rows. There is thus also the possibility to make a number of sensor rows on each substrate. This can be used either to increase the number of selectivity patterns (different sensors in two or more rows) or to obtain a device with redundancy (sensors of the same kind in more than one row) and therefor a better accuracy and long term stability.

Figure 5:
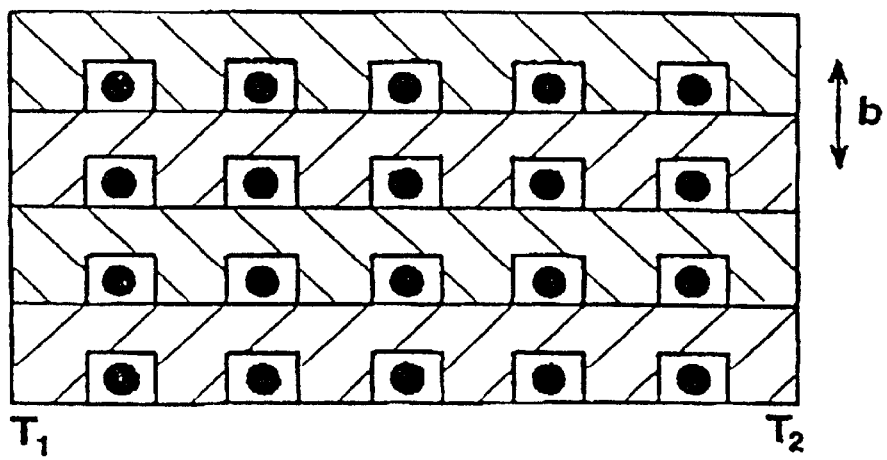
FIG. 5 shows catalyst and sensors on a common substrate.

FIG. 5 shows another interesting possibility, namely the fabrication of the sensor and the catalytic areas on the same substrate. The above mentioned dimensioning rules are still applicable with the addition that in this case, the size of the catalytic areas and the distance between these and the sensors should be small in order to couple the reactions of the catalytic materials efficiently to the sensors. The size of this distance b depends on the reactivity of the catalytic materials and the flow rate of the gas mixture that is analyzed. Typically this distance should be less than a few millimeters. The number of possible combinations and types of patterns is again substantial. The advantage with the arrangement according to FIG. 5 is that the device does not necessarily have to be used in a flow cell. Further, the use of the device as shown in FIG. 5 in a flow cell with a lid with catalytic material, that is, in a configuration similar to that in FIG. 3, is of course also a possibility that further increases the number of selectivity patterns. The device according to FIG. 3a has the advantage that by simply changing the lid with catalytic pattern new selectivity patterns can be obtained with the same sensor matrices as before (or vice versa).

It should be pointed out that other arrangements than the above described are possible. For instance, there is nothing to prevent catalytic materials in the shape of a tube or a helix (in a cylindrical flow cell) to surround the sensor array.

Figure 6A:
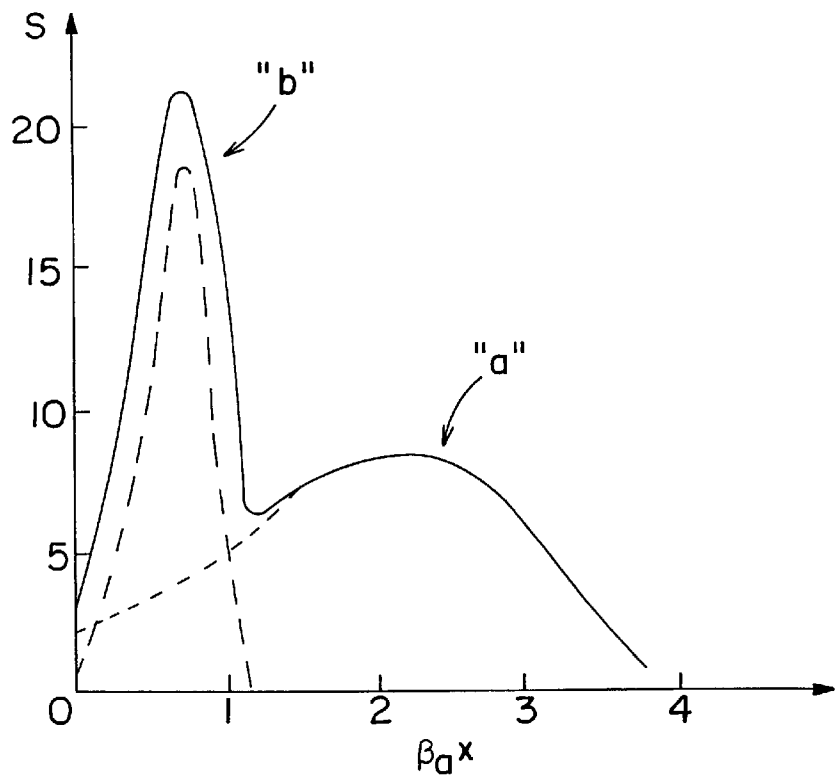
FIG. 6*a* and FIG. 6*c* show the signal response from a device as shown in FIG. 6*b*.
Figure 6B:
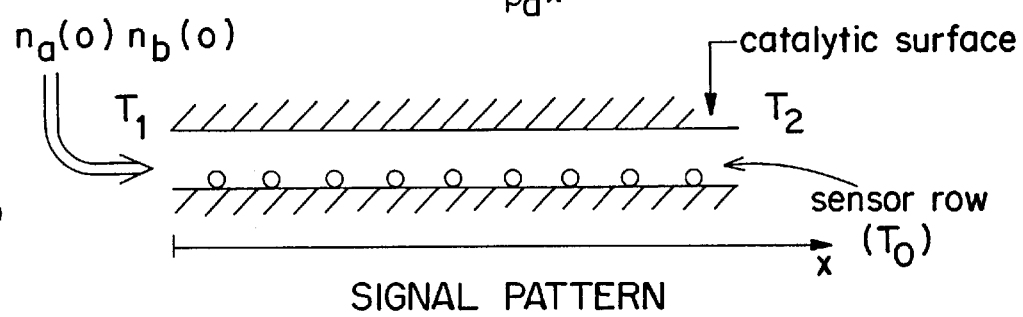
Figure 6C:
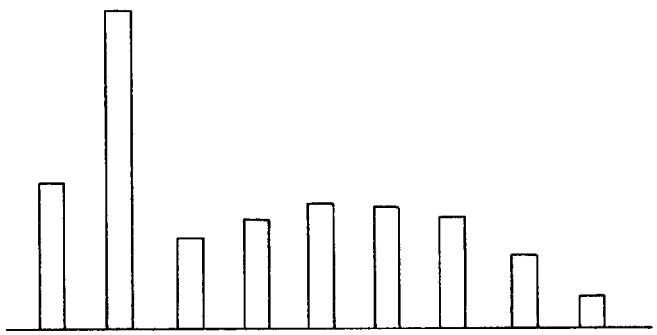

In FIG. 6a simple example is depicted showing the method of the invention. Assume two substances a and b in the gas mixture which are "consumed" on the catalytic surface with a temperature gradient. This will result in a reduction of the number of molecules along the surface of the catalyst depending on the properties of the molecules. The different properties of the molecules will provide different concentration profiles along the catalytic surface. A number of sensors are provided along the bottom surface and the signals from these are dependent on the concentrations of the molecules and the temperature of the sensors. This means that in the signal pattern obtained from the different sensors shown in FIG. 6c, and corresponding to the curves shown in FIG. 6a as calculated, molecules will provide different maxima which can be used to recognize the different molecules present, making the otherwise unselective sensors selective. Of course more than two components may be told apart in this way.

Discrete sensors may be arranged on a catalyst or surrounded by one or indeed several different catalysts in a suitable pattern, for instance strips. At the same time one or several catalysts may be arranged in a suitable pattern opposite to the sensors, for instance in a lid or roof of a sensor cell. This pattern may include strips of different catalysts that may be the same as those surrounding the discrete sensors or different from these, or in any other order. The pattern may also contain strips angled in another direction than the sensors or catalyst strips on the same substrate as the sensors.

The invented way of increased selectivity may be used in combination with known sensors and may in fact be used to improve already fabricated devices.

The invention enables simple adaptation to new odors by changing any combination of catalytic surface, the sensor array, temperature and the temperature gradients along the catalytic surface and sensor array.

Detection in accordance with the invention need not to be static during sensing but may instead be varied, preferably periodically during the sensing procedure. This is very easily achieved by rotating the catalyst top part in a sensing cell. Also the temperature or temperatures of the catalysts and sensors may vary.

The invention provides an increase in available selectivity patterns and the computer may use its own logic to determine the best set up for detection of the various components.

What is claimed is:

1. A modular flow cell for identifying and quantifying gaseous components of a gas mixture, said flow cell including a pair of opposed, exchangeable walls defining in part a flow path through said cell, one of said pair of walls carrying one or an array of gas sensors selected to permit detection and measurement of one or more components of said gas mixture, the wall opposite thereto carrying a catalyst material selected from reacting one or more components of said gas mixture.

2. A module flow cell according to claim 1, wherein the wall carrying the catalyst material has shaped areas of catalyst materials.

3. A module flow cell according to claim 2, wherein said shaped areas of catalyst material are arranged as stripes or bands.

4. A module flow cell according to claim 1, wherein the wall carrying the catalyst material has shaped areas of different catalyst materials.

5. A module flow cell according to claim 1, wherein the wall carrying the sensors has a plurality of sensors arranged in rows in the direction of said flow path.

6. A module flow cell according to claim 1, wherein the wall carrying the sensors has a plurality of sensors arranged transverse to the direction of said flow path.

* * * * *

UNITED STATES PATENT AND TRADEMARK OFFICE
CERTIFICATE OF CORRECTION

PATENT NO. : 6,187,597 B1  
DATED : February 13, 2001  
INVENTOR(S) : Lundstrom et al.

Page 1 of 1

It is certified that error appears in the above-identified patent and that said Letters Patent is hereby corrected as shown below:

<u>Column 6, claim 1,</u>  
Line 27, change "from" to -- for --.

Signed and Sealed this

Nineteenth Day of February, 2002

Attest:

Attesting Officer

JAMES E. ROGAN  
*Director of the United States Patent and Trademark Office*